United States Patent [19]

Kuo

[11] Patent Number: 4,490,546

[45] Date of Patent: Dec. 25, 1984

[54] PROCESS FOR 4A'(R),5'-DIHYDROMEVINOLIN

[75] Inventor: Chan-Hwa Kuo, South Plainfield, N.J.

[73] Assignee: Merck & Co., Inc., Rahway, N.J.

[21] Appl. No.: 506,093

[22] Filed: Jun. 20, 1983

Related U.S. Application Data

[63] Continuation-in-part of Ser. No. 362,018, Mar. 25, 1982, abandoned.

[51] Int. Cl.$^3$ .................................. C07D 309/30
[52] U.S. Cl. ............................................. 549/292
[58] Field of Search ..................................... 549/292

[56] References Cited

U.S. PATENT DOCUMENTS

| | | | |
|---|---|---|---|
| 4,282,155 | 8/1981 | Smith et al. | 549/292 |
| 4,293,496 | 10/1981 | Willard | 549/292 |
| 4,294,846 | 10/1981 | Albers-Schonberg et al. | 424/279 |

OTHER PUBLICATIONS

Albers–Schonberg et al., *J. Antibiotics*, 34, 507–512 (1981).
Prinzbach et al., Agnew. Chem., Int'l. Ed., 14, 753–755 (1975).
Corey et al., *J. Am. Chem. Soc.*, 85, 2677–2678 (1963).

*Primary Examiner*—Norma S. Milestone
*Attorney, Agent, or Firm*—Joseph F. DiPrima; William H. Nicholson

[57] ABSTRACT

Mevinolin is converted to its 4a',5'-dihydro derivative by a route involving protection of the 3',4'-double bond followed by reduction of the 4a',5'-double bond followed by deprotection of the 3',4'-positions.

6 Claims, No Drawings

PROCESS FOR 4A'(R),5'-DIHYDROMEVINOLIN

RELATED APPLICATION

This application is a continuation-in-part of application Ser. No. 362,018, filed Mar. 25, 1982, now abandoned.

BACKGROUND OF THE INVENTION

This invention is concerned with a chemical synthesis of the naturally occurring 4a',5'-dihydromevinolin. Mevinolin is an antihypercholesterolemic agent produced in fermentations with *Aspergillus terreus* as described in U.S. Pat. No. 4,231,938 by Monaghan et al. A 4a',5'-dihydromevinolin is co-produced with mevinolin in considerably lower yield as described in U.S. Pat. No. 4,294,846 by Albers-Schonberg et al. However, this naturally occurring 4a',5'-dihydromevinolin appears to be slightly more active than mevinolin as an HMG-CoA reductase inhibitor. Efforts to convert the more abundant mevinolin to its more active 4a',5'-dihydro derivative have been made by catalytic reduction as reported in published EP application No. 0033537 but yielded only 3',5'-dihydro-, 3',4'-dihydro-, and 3',4',4a',5'-tetrahydro derivatives with no evidence of the desired trans-fused 4a',5'-dihydromevinolin.

Now with the present invention, there is provided a process for the synthesis of the naturally occurring 4a'(R),5'-dihydromevinolin via a route involving protection of the 3',4'-double bond followed by reduction of the 4a',5'-double bond and subsequent deprotection of the 3',4'-positions.

DETAILED DESCRIPTION OF THE INVENTION

The novel process of this invention comprises the following steps, individually and sequentially, of:

(a) t-butyldimethylsilylation of mevinolin 1 by treating it with t-butyldimethylsilyl chloride and an acid acceptor such as an organic amine, alkali metal carbonate, or basic resin in a solvent such as DMF, or HMPA at about 20-50° C. for about 2 to 16 hours to produce 2;

(b) osmium tetroxide hydroxylation of 2 to produce 3 by treating with 2 with $OsO_4$ in a mixture of pyridine and a benzenoid aromatic solvent such as benzene, toluene or the like;

(c) hydrogenation of the 4a',5'-double bond of 3 with hydrogen in the presence of a noble metal hydrogenation catalyst such as platinum oxide, platinum on carbon, palladium on carbon, rhodium or alumina or Raney nickel, especially platinum oxide in a solvent such as ethyl acetate to produce the cis glycol 4 with the trans decalin ring juncture;

(d) cyclic thionocarbonate formation to give 5, by treatment of 4 with 1,1'-thiocarbonyldiimidazole in a benzenoid aromatic solvent such as benzene or toluene at about 50° to 100° C. for about 15 to 60 minutes;

(e) conversion of the thionocarbonate 5 to the silylated olefin 6 by treatment of 5 with triethylphosphite at reflux temperature for about 100 to 200 hours; and (f) hydrolysis of the t-butyldimethylsilyl ether 6 with dilute mineral acid such as hydrochloric acid, sulfuric acid, phosphoric acid or the like in a solvent or mixture of solvents such as acetic acid, THF, tetrahydropyran, 1,2-dimethoxyethane or the like to produce 4a'(R),5'-dihydromevinolin 7.

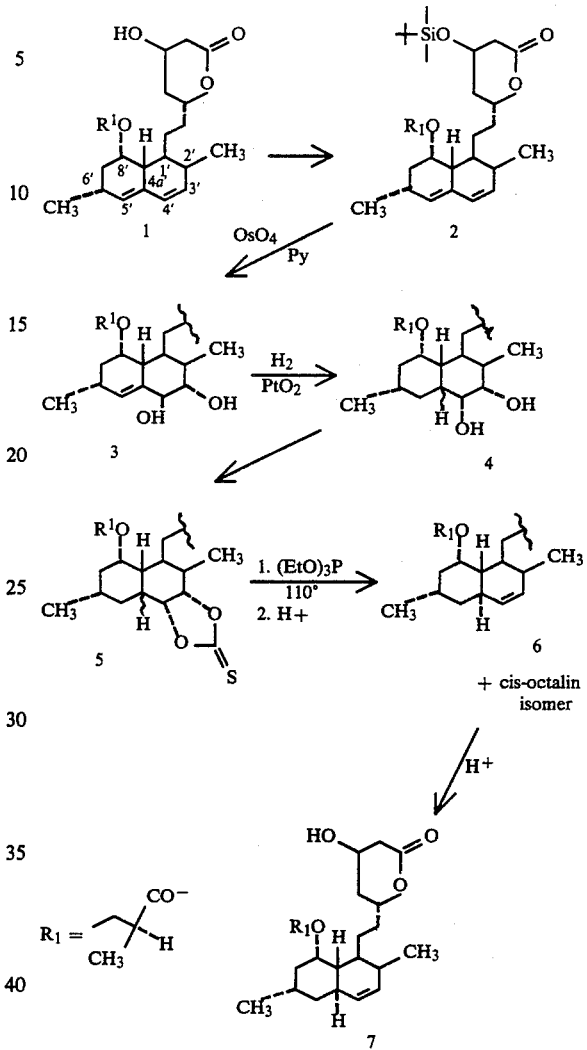

The compound of the novel process of this invention is highly useful as an antihypercholesteolemic agent for the treatment of atherosclerosis, hyperlipemia and like diseases in humans. It may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compound also has useful antifungal activities. For example, it may be used to control strains of Penicillium sp., *Aspergillus niger*, Cladosporium sp., *Cochliobolus miyabeanus* and *Helminthosporium cynodnotis*. For those utilities it is admixed with suitable formulating agents, powders, emulsifying agents or solvents such as aqueous ethanol and sprayed or dusted on the plants to be protected.

EXAMPLE

(a) t-Butyldimethylsilylation of Mevinolin

Mevinolin 1 (1.556 g, 2.857 mmol), t-butyldimethylsilyl chloride (1.2917 g, 8.57 mmol), and imidazole (1.2157 g, 17.856 mmol) in 10 ml of dry dimethylformamide was heated at 35° under nitrogen for 5 hours. The mixture was diluted with a large volume of a mixture of ethyl acetate-benzene (1:1) and washed with water several times. The organic phase was dried over anhydrous $Na_2SO_4$ and evaporated in vacuo to 1.48 g of 2 as an oil. NMR ($CDCl_3$) δ: 0.1 (s, 6H), 0.9 (s), 2.58 (d, J=4 Hz), 4.30 (m, 1H), 4.60 (m, 1H), 5.35 (m, 1H), 5.57 (m, 1H), 5.7–6.2 (m, 2H). Ms m/z 518 (M+), 359, 341, 284.

(b) $OsO_4$-Hydroxylation of 2

A solution of osmium tetroxide (0.6502 g, 2.558 mmol) in dry pyridine (2 ml) was added dropwise to a stirred solution of the silyl derivative 2 (1.327 g, 2.558 mmol) in a mixture of benzene (4 ml) and pyridine (2 ml) at 5° under nitrogen. A dark brown mixture formed almost instantaneously after the addition was complete. The mixture was stirred at 25° for 16 hours, followed by addition of a chilled solution of sodium bisulfite (1.171 g) in $H_2O$ (19 ml) and pyridine (13 ml) to give a brown precipitate. After stirring at room temperature for 1.5 hours, the mixture was evaporated in vacuo and extracted with ethylacetate. The organic phase was washed with water, salt solution, dried over anhydrous $Na_2SO_4$ and concentrated to 2.03 g of a residue. Chromatographic purification and elution with 30% acetone in chloroform, provided 504.8 mg of the unreacted starting material 2 and 320 mg of the tetrol 3a, m.p. 180°–181°, and 567 mg of the glycol 3, IR ($CHCl_3$) 3580–3300, 1725 cm$^{-1}$. NMR ($CDCl_3$) δ 0.1 (6H), 0.9 (s), 2.57 (d, J=4 Hz), 3.83 (m, 1H), 4.1–4.9 (m, 3H), 5.33 (m, 1H), 5.90 (m, 1H), ms m/z 552 (M+), 477, 450, 432 and 393.

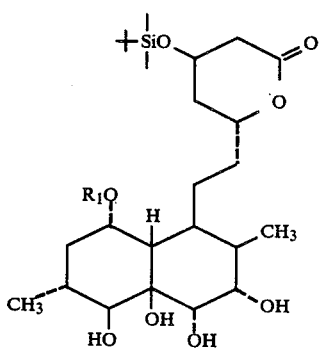

3a

(c) Hydrogenation of 3

A solution of the glycol 3 (565 mg, 1.022 mmol) in ethyl acetate (15 ml) was hydrogenated at room temperature under 1 atm of hydrogen with an equal amount by weight of platinum oxide as catalyst. The uptake of hydrogen ceased after 1 hour. The catalyst was removed by filtration and the solvent was evaporated in vacuo to yield 570 mg of a foam, 4, as a mixture having the cis and trans decalin ring juncture. IR ($CHCl_3$) 3650–3300, 1721 cm. NMR ($CDCl_3$) δ 0.1 (s, 6H), 0.9 (s), 2.57 (d, J=4 Hz), 3.77 (m, 2H), 4.3 (m), 4.4–5.2 (m, 2H). Ms m/z 554 (M+), 536, 524, 452, 434.

(d) Cyclic thionocarbonate formation to give 5

A mixture of the saturated glycol 4 (146.8 mg, 0.2646 mmol), 1,1'-thiocarbonyldiimidazole (70.74 mg, 0.3969 mmol) in 2 ml of dry toluene was refluxed for 30 minutes. After removal of the solvent at reduced pressure, the residue was extracted into methylene chloride and washed with water and salt solution. The organic phase was dried over anhydrous $Na_2SO_4$ and evaporated to dryness. Preparative layer chromatography (5% acetone in chloroform, $R_f=0.42$) provided the cyclic thionocarbonate 5 (118 mg, 75.4% of theory). Ms m/z 596 (M+), 537. NMR ($CDCl_3$): δ 0.1 (s, 6H), 0.9 (s), 2.57 (d, J=4 Hz). 4.15–5.3 (m, 5H).

(e) Conversion of thionocarbonate 5 to silylated olefin 6

A mixture of the cyclic thionocarbonate 5 (101 mg, 0.169 mmol) and triethylphosphite (2.5 ml) was heated at reflux under nitrogen for 140 hours. The solvent was removed in vacuo and preparative layer chromatography of the residue (2% acetone in chloroform as the eluting solvent) provided 56 mg of an olefin (63% of theory). Infrared spectrum showed the absence of hydroxyl functionality; ester carbonyl group appeared as a strong band at 1720 cm$^{-1}$. Ms m/z 521 (M+), 464, 418. NMR ($CDCl_3$) δ 0.1 (s, 6H), 0.9 (s), 2.6 (d, J=4 Hz), 4.2–5.3 (m, 3H), 5.58 (dd, J=10 Hz, 2H).

(f) Hydrolysis to 4a',5'-dihydromevinolin

The monoolefin silyl ether obtained above (50 mg, 0.096 mmol) was stirred at room temperature in a mixture of 1.5 ml of acetic acid:water:tetrahydrofuran (3:1:1), plus one drop of 2.5N aq. hydrochloric acid. Progress of the hydrolysis was monitored by TLC. After 9 hours the reaction mixture no longer contained starting material and was evaporated in vacuo to dryness; preparative layer chromatography produced the cis alcohol (28.5 mg), ms m/z 406 (M+), 304, 286. NMR ($CDCl_3$) δ 0.7–2.5 (m, 33H), 2.7 (d, J=5 Hz, 2H), 4.2–5.12 (m, 3H), 5.58 (m, J=9.8 Hz, 2H). 300 MHz $^1$Hnmr displayed vicinal coupling constants of 4.6 and 4.8 Hz between the vinyl protons and protons at 2' and 4a' positions. Each olefinic hydrogen appeared as a double of doublet in benzene solution.

The trans alcohol 7 (4.0 mg), ms m/z 304, 286; 300 MHz $^1$Hnmr in $C_6D_6$ showed coupling constants of near zero and 5 Hz, respectively, between the vinyl protons and protons at 2' and 4a' positions as a double of doublet.

What is claimed is:

1. A process for the preparation of trans 4a',5'-dihydromevinolin comprising the steps of:
 (a) t-butyldimethylsilylation of mevinolin with t-butyldimethylsilyl chloride and an acid acceptor at about 20°–50° C. for about 2 to 16 hours to produce 2;

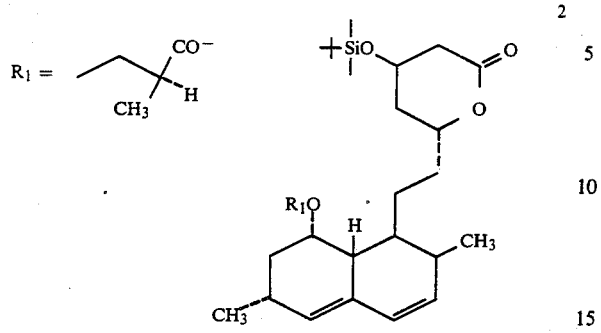

(b) osmium tetroxide hydroxylation of 2 to produce 3 by treating 2 with OsO$_4$ in a mixture of pyridine base and a benzenoid aromatic solvent;

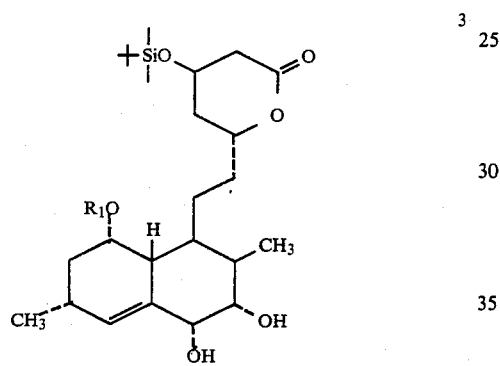

(c) hydrogenation of the 4a′,5′-double bond of 3 with hydrogen in the presence of a noble metal hydrogenation catalyst in a solvent to produce the glycol 4;

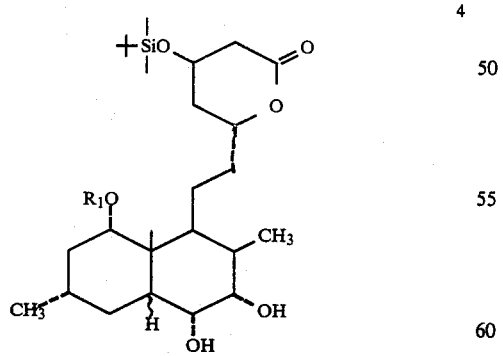

(d) cyclic thionocarbonate formation to give 5, by treatment of 4 with 1,1′-thiocarbonyldiimidazole in a benzenoid aromatic solvent at about 50°–100° C. for about 15 to 60 minutes;

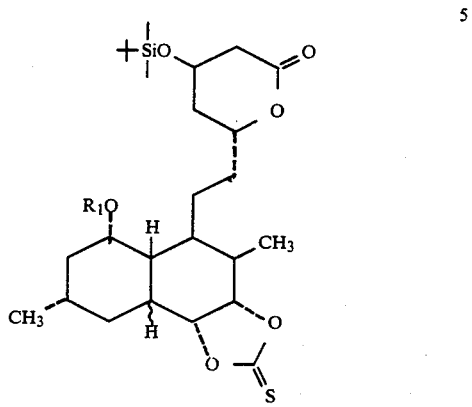

(e) conversion of the thionocarbonate 5 to the silylated olefin 6 by treatment of 5 with triethylphosphite at reflux temperature for about 100 to 200 hours;

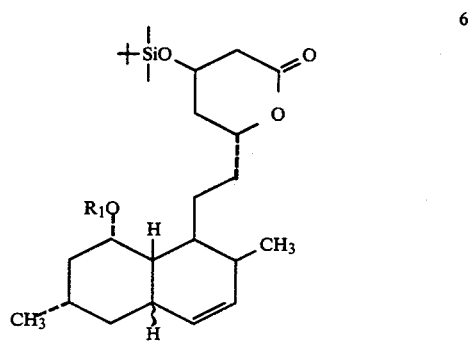

(f) hydrolysis of the t-butyldimethylsilyl ether 6 with dilute mineral acid in a solvent to produce 4a′(R),5′-dihydromevinolin 7

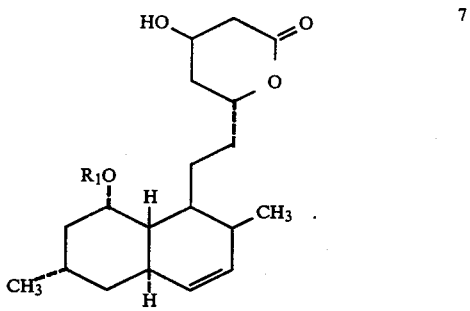

2. The process for the preparation of trans 4a′,5′-dihydromevinolin comprising the steps of:

(a) osmium tetroxide hydroxylation of 2

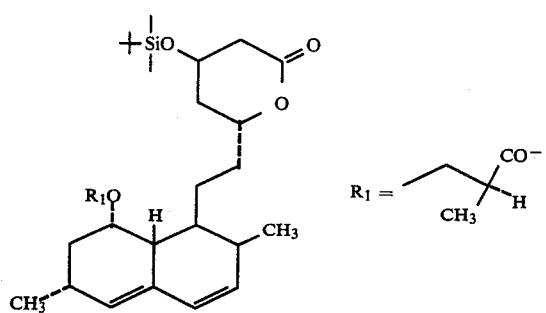

to produce 3 by treating 2 with $OsO_4$ in pyridine and a benzenoid aromatic solvent;

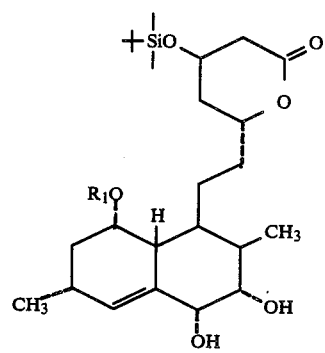

(b) hydrogenation of the 4a′,5′-double bond of 3 with hydrogen in the presence of a noble metal hydrogenation catalyst in a solvent to produce the glycol 4;

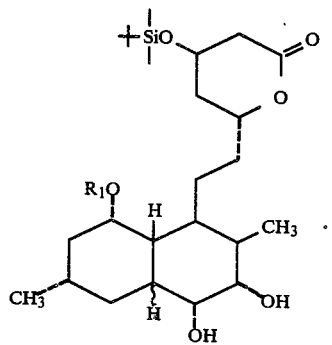

(c) cyclic thionocarbonate formation to give 5, by treatment of 4 with 1,1′-thiocarbonyldiimidazole in a benzenoid aromatic solvent at about 50° to 100° C. for about 15 to 60 minutes;

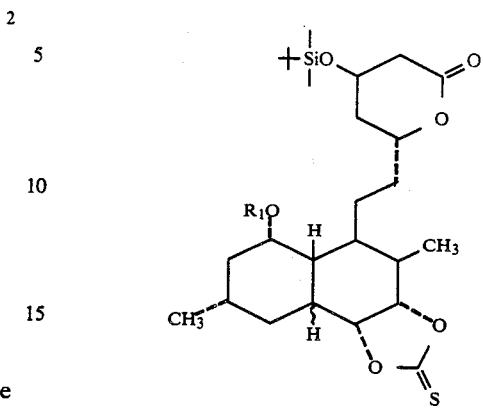

(d) conversion of the thionocarbonate 5 to the silylated olefin 6 by treatment of 5 with triethylphosphite at reflux temperature for about 100 to 200 hours;

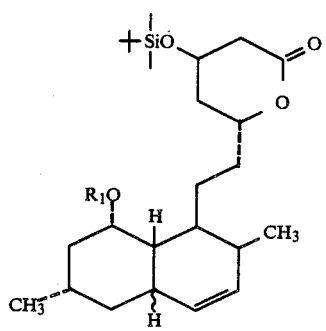

(e) hydrolysis of the t-butyldimethylsilyl ether 6 with dilute mineral acid in a solvent to produce 4a′(R),5′-dihydromevinolin 7

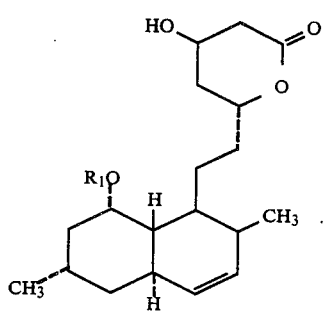

3. The process for the preparation of trans 4a′,5′-dihydromevinolin comprising the steps of:

(a) hydrogenation of the 4a′,5′-double bond of 3

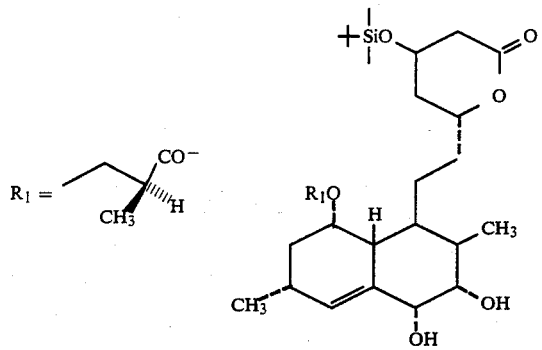

with hydrogen in the presence of a noble metal hydrogenation catalyst in a solvent to produce the glycol 4;

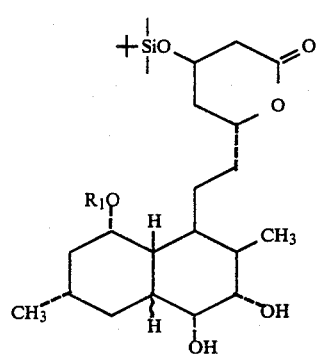

(b) cyclic thionocarbonate formation to give 5, by treatment of 4 with 1,1'-thiocarbonyldiimidazole in a benzenoid aromatic solvent at about 50° to 100° C. for about 15 to 60 minutes;

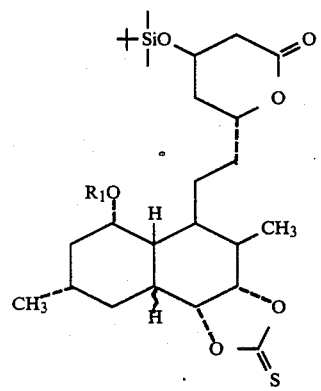

(c) conversion of the thionocarbonate 5 to the silylated olefin 6 by treatment of 5 with triethylphosphite at reflux temperature for about 100 to 200 hours;

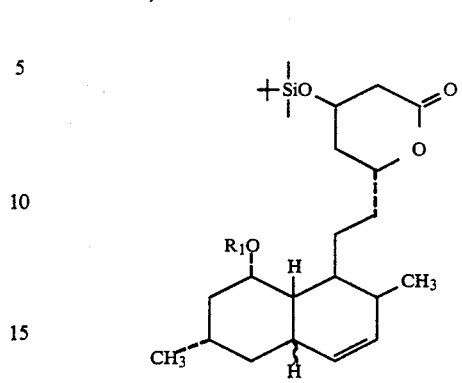

(d) hydrolysis of the t-butyldimethylsilyl ether 6 with dilute mineral acid in a solvent to produce 4a'(R),5'-dihydromevinolin 7

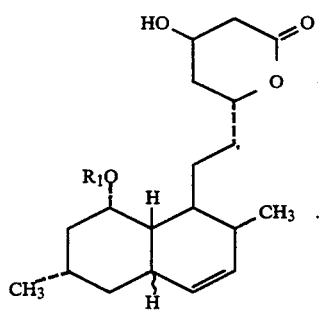

4. The process of claim 1 wherein: in Step (a) the acid acceptor is an organic base and the solvent is DMF; in Step (b) the benzenoid aromatic solvent is benzene; in Step (c) the catalyst is selected from platinum oxide, platinum on carbon, palladium on carbon, and Raney nickel; in Step (d) the benzenoid aromatic solvent is benzene; in Step (f) the hydrolysis is conducted with a mixture of acetic acid, THF and dilute hydrochloric acid.

5. The process of claim 2 wherein: in Step (a) the benzenoid aromatic solvent is benzene; in Step (b) the catalyst is selected from platinum oxide, platinum on carbon, palladium on carbon, and Raney nickel; in Step (c) the benzenoid aromatic solvent is benzene; in Step (e) the hydrolysis is conducted with a mixture of acetic acid, THF and dilute hydrochloric acid.

6. The process of claim 3 wherein in Step (a) the catalyst is selected from platinum oxide, platinum on carbon, palladium on carbon, and Raney nickel; in Step (b) the benzenoid aromatic solvent is benzene; in Step (d) the hydrolysis is conducted with a mixture of acetic acid, THF and dilute hydrochloric acid.

* * * * *